United States Patent [19]

Eidenschink et al.

[11] Patent Number: 4,659,503
[45] Date of Patent: Apr. 21, 1987

[54] PYRIDYLTHIOPHENES

[75] Inventors: Rudolf Eidenschink, Münster; Bernhard Scheuble, Alsbach, both of Fed. Rep. of Germany

[73] Assignee: Merck Patent Gesellschaft Mit Beschränkter Huftung, Darmstadt, Fed. Rep. of Germany

[21] Appl. No.: 685,083

[22] Filed: Dec. 21, 1984

[30] Foreign Application Priority Data

Dec. 21, 1983 [DE] Fed. Rep. of Germany ....... 3346175

[51] Int. Cl.$^4$ .......................... C09K 3/34; G02F 1/13; C07D 409/04; C07D 409/14
[52] U.S. Cl. ........................ 252/299.61; 252/299.5; 350/350 R; 350/350 S; 546/280; 546/276; 546/193; 546/194; 544/333; 544/316; 544/318; 544/298
[58] Field of Search ...................... 546/280; 252/299.5, 252/299.61, 299.63; 350/350 R, 350 S

[56] References Cited

U.S. PATENT DOCUMENTS 4,175,195 11/1979 Deschke et al. ................... 546/250
4,510,069 4/1985 Eidenschink et al. ......... 252/299.63

FOREIGN PATENT DOCUMENTS

| 87629 | 9/1983 | European Pat. Off. ....... 252/299.61 |
| 3342631 | 6/1985 | Fed. Rep. of Germany ....................... 252/299.61 |
| 158480 | 1/1983 | German Democratic Rep. ....................... 252/299.61 |
| 55-151077 | 11/1980 | Japan ............... 252/299.61 |
| 58-121272 | 7/1983 | Japan ............... 252/299.61 |
| 60-149564 | 8/1985 | Japan ............... 252/299.61 |
| 2130580 | 6/1984 | United Kingdom . |
| 1069413 | 4/1985 | U.S.S.R. ................ 252/299.61 |
| 1063101 | 6/1985 | U.S.S.R. ................ 252/299.61 |

OTHER PUBLICATIONS

Kaeamysheva, L. A., et al., Mol. Cryst. Liq. Cryst., vol. 67, pp. 241-252 (1981).
Grachev, V. T., et al. Mol. Cryst. Liq. Cryst., vol. 65, pp. 133-144 (1981).
Dewar, M. J. S., et al., Liquid Crystals and Ordered Fluids, vol. 2, Johnson, J. et al., Ed., Plenum Press, N.Y., pp. 733-741 (1980).
Pavluchenko, A. I., et al., Advances in Liquid Crystal Research & Applications, Bata, L., Ed., Pergamon Press, Oxford, pp. 1007-1013 (1980).
Osmam, M. A., et al., Mol. Cryst. Liq. Cryst., vol. 82 (Letters), pp. 339-344 (1983).
Nash, J. A., et al., Mol. Cryst. Liq. Cryst., vol. 25, pp. 299-321 (1974).
Pavluchenko, A. I., et al., J. De Physique, vol. 4, Coll. C3, Suppl. No. 4, pp. C3-1-4 (1979).
Vernin et al., "Homolytic", J. Org. Chem., vol. 40, No. 22, 1975, pp. 3183-3189.
Chemical Abstracts, vol. 95, No. 17, 1981, p. 639.
Chemical Abstracts, vol. 95, No. 24, 1981, p. 649.
Kaeamysheve, et al, Molecular Crystals and Liquid Crystals, Jul. 1980.

*Primary Examiner*—Teddy S. Gron
*Attorney, Agent, or Firm*—Millen & White

[57] ABSTRACT

Liquid crystal compounds containing the structural constituent —Py—Th—, wherein Py is a pyridine-2,5-diyl ring and Th is a thiophene-2,4- or -2,5-diyl ring, and in particular pyridylthiophenes of the formula I

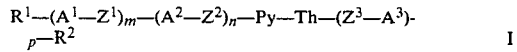

$$R^1{-}(A^1{-}Z^1)_m{-}(A^2{-}Z^2)_n{-}Py{-}Th{-}(Z^3{-}A^3)_p{-}R^2 \qquad I$$

wherein Py and Th have the meanings given, $R^1$ and $R^2$ are each an alkyl group with 1-15 C atoms, in which one or two $CH_2$ groups can also be replaced by O atoms; F, Cl, Br, CN or —O—COR, and one of these radicals can also be H, $A^1$, $A^2$ and $A^3$ are each 1,4-phenylene, 1,4-cyclohexylene, 1,3-dioxane-2,5-diyl, piperidine-1,4-diyl, 1,4-bicyclo-(2,2,2)-octylene or pyrimidine-2,5-diyl groups which are unsubstituted or substituted by 1–4 F atoms, it being possible for the cyclohexylene group(s) to be substituted in the 1- and/or 4-position by alkyl, alkoxy, fluorinated alkyl or fluorinated alkoxy with in each case 1-5 C atoms, F, Cl, Br and/or CN, $Z^1$, $Z^2$ and $Z^3$ are each —CO—O—, —O—CO—, —$CH_2CH_2$—, —$OCH_2$—, —$CH_2O$— or a single bond, (m+n+p) is 0, 1 or 2 and R is an alkyl group with 1-5 C atoms, and the acid addition salts of the basic compounds of this type, are suitable as constituents of liquid crystal phases.

25 Claims, No Drawings

PYRIDYLTHIOPHENES

BACKGROUND OF THE INVENTION

This invention relates to new compounds having valuable liquid crystalline properties.

SUMMARY OF THE INVENTION

It is an object of this invention to provide new compounds useful as liquid crystalline components.

It is another object of this invention to provide new stable liquid crystal or mesogenic compounds which are suitable as components of liquid crystal dielectrics.

These objects have been achieved by providing new liquid crystal compounds containing the structural consituent —Py—Th—, wherein Py is a pyridine-2,5-diyl ring and Th is a thiophene-2,4- or 2,5-diyl ring, and in particular pyridylthiophenes of the formula I $$R^1-(A^1-Z^1)_m-(A^2-Z^2)_n-Py-Th-(Z^3-A^3)_p-R^2 \quad \text{I}$$

wherein Py is a pyridine-2,5-diyl ring, Th is a thiophene-2,4-or -2,5-diyl ring, $R^1$ and $R^2$ are each an alkyl group with 1-15 C atoms, in which one or two non-adjacent $CH_2$ groups can also be replaced by O atoms, F, Cl, Br, CN or —O—COR, and one of these radicals can also be H, $A^1$, $A^2$ and $A^3$ are each 1,4-phenylene, 1,4-cyclohexylene, 1,3-dioxane-2,5-diyl, piperidine-1,4-diyl, 1,4-bicyclo-(2,2,2)-octylene or pyrimidine-2,5-diyl groups which are unsubstituted or substituted by 1-4 F atoms, it being possible for the cyclohexylene group(s) to be substituted in the 1- and/or 4-position by alkyl, alkoxy, fluorinated alkyl or fluorinated alkoxy with in each case 1-5 C atoms, F, Cl, Br and/or CN, $Z^1$, $Z^2$ and $Z^3$ are each —CO—O—, —O—CO—, —CH$_2$CH$_2$—, —OCH$_2$—, —CH$_2$O— or a single bond, (m+n+p) is 0, 1 or 2 and R is an alkyl group with 1-5 C atoms, and the acid addition salts of the basic compounds of this type.

For simplicity, in the following text "Phe" is a 1,4-phenylene group, "Cy" is a 1,4-cyclohexylene group, "Dio" is a 1,3-dioxane-2,5-diyl group, "Bic" is a bicyclo-(2,2,2)-octylene group, "Pip" is a piperidine-1,4-diyl group and "Pyr" is a pyrimidine-2,5-diyl group, it being possible for these groups to be unsubstituted or substituted as described above for the definition of $A^1$, $A^2$ and $A^3$.

Like similar compounds, the compounds of the formula I can be used as components of liquid crystal dielectrics, in particular for displays based on the principle of the twisted cell, the guest-host effect, the 2-frequency method, electrically controlled double refraction or the effect of dynamic scattering.

It has been found that the compounds of the formula I are outstandingly suitable as components of liquid crystal dielectrics. In particular, stable liquid crystal phases with very different dielectric anisotropy and hence a threshold or control voltage of electrooptical effects which can be varied within wide limits, variable optical anisotropy and a comparatively low viscosity can be prepared with the aid of these compounds.

Surprisingly, it has been found that when compounds of the formula I are added to mixtures with positive dielectric anisotropy, even the addition of relatively large amounts (for example 30%) of compounds of the formula I with negative dielectric anisotropy causes only an insignificant increase in the threshold voltage. At the same time, a considerable improvement in the steepness of the characteristics line of the mixture occurs completely unexpectedly, so that compounds of Formula I are to be regarded as substances which are particularly advantageously suitable for the preparation of liquid crystal mixtures with a steep characteristic line. They thus allow the development of highly multiplexible mixtures.

By providing the compounds of the formula I, the range of liquid crystal substances which are suitable for the preparation of nematic mixtures from various technological viewpoints is also quite generally considerably extended.

The compounds of the formula I have a wide range of application. Depending on the choice of the substituents, these compounds can be used as the base materials of which liquid crystal dielectrics are predominantly composed. However, it is also possible to add compounds of the formula I to liquid crystal base materials from other classes of compounds, for example in order to modify the dielectric and/or optical anisotropy or the mesophase range of such a dielectric. The compounds of the formula I are furthermore suitable as intermediates for the preparation of other substances which can be used as constituents of liquid crystal dielectrics.

The compounds of the formula I are colorless in the pure state and form liquid crystal mesophases in a temperature range which is advantageously placed for electrooptical use. They are sufficiently stable towards chemicals, heat and light.

More generally, this invention as described above pertains in a liquid crystalline phase comprising at least two liquid-crystal components, wherein at least one is a compound having the structure, wing group-(ring-bridging element)-ring A-(bridging element-ring)-wing group, wherein the wing groups, the bridging elements and the rings are conventional structural elements in liquid crystal comounds, and wherein the structural components comprising a ring and a bridging element are optional, up to two such components in total being possible, and the wing groups, rings and bridging elements being the same or different, to the improvement wherein structural feature ring A is of the formula —Py—Th, wherein Py is pyridine-2,5-diyl and Th is thiophene-2,4- or 2,5-diyl.

DETAILED DISCUSSION

Throughout the text, "compounds of formula I" is intended to include all compounds within the scope of this invention.

The invention thus relates to the compounds of the formula I and to a process for their preparation, characterised in that a compound of the formula II is reacted with a compound of the formula III $$R^1-(A^1-Z^1)_m-(A^2-Z^2)_n-Py-Q^1 \quad \text{II}$$

$$Q^2-Th-(Z^3-A^3)_p-R^2 \quad \text{III}$$

wherein either one of the radicals $Q^1$ and $Q^2$ is one equivalent of a metal atom or the MgHal group, the other of these radicals is F, Cl, Br or I and Hal is Cl, Br or I, or one of the radicals $Q^1$ and $Q^2$ is a diazonium salt group or an N-nitroso-acylamino group and the other of these radicals is H, and Py, Th, $R^1$, $A^1$, $A^2$, $A^3$, $Z^1$, $Z^2$, $Z^3$, m, n and p have the meanings given above, or in that a compound which otherwise corresponds to the formula I but contains one or more reducible groups and- /or C—C bonds instead of H atoms is treated with a reducing agent, or in that, for the preparation of esters of the formula I (wherein $R^1$ and/or $R^2$ are —O—COR and/or wherein $Z^1$ and/or $Z^2$ and/or $Z^3$ are —CO—O— or —O—CO—), a corresponding carboxylic acid or one of its reactive derivatives is reacted with a corresponding alcohol or one of its reactive derivatives, or in that, for the preparation of dioxane derivatives of the formula I (wherein $A^1$ and/or $A^2$ and/or $A^3$ are 1,3-dioxane-2,5-diyl), a corresponding aldehyde is reacted with a corresponding diol, or in that, for the preparation of nitriles of the formula I (wherein $R^1$ and/or $R^2$ are CN and/or wherein $A^1$ and/or $A^2$ and/or $A^3$ are substituted by at least one CN group), a corresponding carboxylic acid amide is dehydrated or a corresponding carboxylic acid halide is reacted with sulfamide, or in that, for the preparation of ethers of the formula I (wherein $R^1$ and/or $R^2$ are an alkyl group, in which one or two $CH_2$ groups are replaced by O atoms, and/or $Z^1$ and/or $Z^2$ and/or $Z^3$ are a —$OCH_2$— or —$CH_2O$— group), a corresponding hydroxy compound is etherified, and/or in that, for the preparation of chlorine or bromine compounds of the formula I (wherein $R^1$ and/or $R^2$ are Cl or Br), a corresponding compound of the formula I (wherein $R^1$ and/or $R^2$ are H) is treated with a chlorinating or brominating agent, and/or in that, if appropriate, a chlorine or bromine compound of the formula I (wherein $R^1$ and/or $R^2$ are Cl or Br and/or wherein $A^1$ and/or $A^2$ and/or $A^3$ are substituted by at least one chlorine or bromine atom) is reacted with a cyanide, and/or in that, if appropriate, a base of the formula I is converted into one of its acid addition salts by treatment with an acid, or in that, if appropriate, a compound of the formula I is liberated from one of its acid addition salts by treatment with a base.

The invention also relates to the use of the compounds of the formula I as components of liquid crystal phases. The invention moreover relates to liquid crystal phases containing at least one compound of the formula I and to liquid crystal display elements and electrooptical display elements containing such phases.

Above and below, Py, Th, $R^1$, $R^2$, $A^1$, $A^2$, $A^3$, $Z^1$, $Z^2$, $Z^3$, m, n, p, R, $Q^1$, $Q^2$ and Hal have the meanings, given above, unless expressly indicated otherwise.

The compounds of the formula I include compounds of the part formulae Ia (with two rings), Ib and Ic (with three rings in each case) and Id and Ie (with four rings):

| | |
|---|---|
| $R^1$—Py—Th—$R^2$ | Ia |
| $R^1$—$A^1$—$Z^1$—Py—Th—$R^2$ | Ib |
| $R^1$—Py—Th—$Z^3$—$A^3$—$R^2$ | Ic |
| $R^1$—$A^1$—$Z^1$—Py—Th—$Z^3$—$A^3$—$R^2$ | Id |
| $R^1$—$A^1$—$Z^1$—$A^2$—$Z^2$—Py—Th—$R^2$ | Ie |

Compounds of the part formula Ia are particularly preferred. The part formulae Ib and Ic, which are furthermore preferred, include compounds of the part formulae Iba to Ibf and Ica to Icf:

| | |
|---|---|
| $R^1$—Phe—$Z^1$—Py—Th—$R^2$ | Iba |
| $R^1$—Cy—$Z^1$—Py—Th—$R^2$ | Ibb |
| $R^1$—Dio—$Z^1$—Py—Th—$R^2$ | Ibc |
| $R^1$—Pip—$Z^1$—Py—Th—$R^2$ | Ibd PS |
| $R^1$—Bic—$Z^1$—Py—Th—$R^2$ | Ibe |
| $R^1$—Pyr—$Z^1$—Py—Th—$R^2$ | Ibf |
| $R^1$—Py—Th—$Z^3$—Phe—$R^2$ | Ica |
| $R^1$—Py—Th—$Z^3$—Cy—$R^2$ | Icb |
| $R^1$—Py—Th—$Z^3$—Dio—$R^2$ | Icc |
| $R^1$—Py—Th—$Z^3$—Pip—$R^2$ | Icd |
| $R^1$—Py—Th—$Z^3$—Bic—$R^2$ | Ice |
| $R^1$—Py—Th—$Z^3$—Pyr—$R^2$ | Icf |

Of these, those of the formulae Iba, Ibb, Ica and Icb are particularly preferred.

In the compounds of the formulae above and below, $R^1$ and $R^2$ are preferably alkyl, or furthermore alkoxy (especially if these radicals are on a Phe group) or another oxaalkyl group.

$A^1$, $A^2$ and $A^3$ are preferably Cy or Phe, and furthermore preferably Dio or Pip; the compound of the formula I preferably contains not more than one of the radicals Dio, Pip, Bic or Pyr.

Cy is preferably an unsubstituted 1,4-cyclohexylene group, and furthermore a 1—X—1,4-cyclohexylene group which carries no further substituents and wherein X is alkyl, alkoxy, fluorinated alkyl or fluorinated alkoxy with in each case 1-5 C atoms, F, Cl, Br or CN. X is preferably a CN, $CH_3$, $CH_3O$ or $CF_3$ group.

$Z^1$, $Z^2$ and $Z^3$ are preferably single bonds, or, secondarily, preferably —CO—O— or —O—CO— groups.

Each individual parameter m, n and p can be 0, 1 or 2. Their sum is in all cases also 0, 1 or 2, preferably 0.

If $R^1$ and/or $R^2$ are alkyl radicals in which one ("alkoxy" or "oxaalkyl") or two ("alkoxyalkoxy" or "dioxaalkyl") $CH_2$ groups can also be replaced by O atoms, they can be straight-chain or branched. Preferably, they are straight-chain and have 2, 3, 4, 5, 6 or 7 C atoms, and accordingly are preferably ethyl, propyl, butyl, pentyl, hexyl, heptyl, ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy, tetradecoxy, pentadexoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formulae I and Ia to Icf with branched end groups $R^1$ and/or $R^2$ may sometimes be of importance because of a better solubility in the usual liquid crystal base materials, but especially as chiral doping substances, if they are optically active. Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

The alkyl groups or alkoxy groups in the radicals R and X are likewise preferably straight-chain and are, in particular, methyl or ethyl, and furthermore propyl, butyl or pentyl, and X can also be methoxy or ethoxy, and furthermore propoxy, butoxy or pentoxy.

The 1-4 F substituents on the $A^1$, $A^2$ and/or $A^3$ groups can be located on any of the available lateral positions on these rings and also in the 1- or 4- positions if this is structurally possible.

The fluorination on the alkyl or alkoxy groups which can be substituted on the 1- and/or 4- positions of the cyclohexylene rings can include any degree from 1 F atom up to perfluorination.

Preferred compounds of the formulae I and Ia to Icf are those in which at least one of the radicals contained therein has one of the preferred meanings mentioned. Particularly preferred smaller groups of compounds are those of the formulae If to Izm:

| | |
|---|---|
| $R^1$—Phe—Py—Th—$R^2$ | If |
| $R^1$—Phe—CO—O—Py—Th—$R^2$ | Ig |
| $R^1$—Phe—O—CO—Py—Th—$R^2$ | Ih |
| $R^1$—Phe—CH$_2$CH$_2$—Py—Th—$R^2$ | Ii |
| $R^1$—Phe—O—CH$_2$—Py—Th—$R^2$ | Ij |
| $R^1$—Phe—CH$_2$—O—Py—Th—$R^2$ | Ik |
| $R^1$—Cy—Py—Th—$R^2$ | Il |
| $R^1$—Cy—CO—O—Py—Th—$R^2$ | Im |
| $R^1$—Cy—O—CO—Py—Th—$R^2$ | In |
| $R^1$—Cy—CH$_2$CH$_2$—Py—Th—$R^2$ | Io |
| $R^1$—Cy—O—CH$_2$—Py—Th—$R^2$ | Ip |
| $R^1$—Cy—CH$_2$—O—Py—Th—$R^2$ | Iq |
| $R^1$—Dio—Py—Th—$R^2$ | Ir |
| $R^1$—Pip—Py—Th—$R^2$ | Is |
| $R^1$—Bic—Py—Th—$R^2$ | It |
| $R^1$—Pyr—Py—Th—$R^2$ | Iu |
| $R^1$—Phe—Phe—Py—Th—$R^2$ | Iv |
| $R^1$—Py—Th—Phe—$R^2$ | Iw |
| $R^1$—Py—Th—CO—O—Phe—$R^2$ | Ix |
| $R^1$—Py—Th—O—CO—Phe—$R^2$ | Iy |
| $R^1$—Py—Th—CH$_2$CH$_2$—Phe—$R^2$ | Iz |
| $R^1$—Py—Th—O—CH$_2$—Phe—$R^2$ | Iza |
| $R^1$—Py—Th—CH$_2$—O—Phe—$R^2$ | Izb |
| $R^1$—Py—Th—Cy—$R^2$ | Izc |
| $R^1$—Py—Th—CO—O—Cy—$R^2$ | Izd |
| $R^1$—Py—Th—O—CO—Cy—$R^2$ | Ize |
| $R^1$—Py—Th—CH$_2$CH$_2$—Cy—$R^2$ | Izf |
| $R^1$—Py—Th—O—CH$_2$—Cy$^9$—$R^2$ | Izg |
| $R^1$—Py—Th—CH$_2$—O—Cy—$R^2$ | Izh |
| $R^1$—Py—Th—Dio—$R^2$ | Izi |
| $R^1$—Py—Th—Pip—$R^2$ | Izj |
| $R^1$—Py—Th—Bic—$R^2$ | Izk |
| $R^1$—Py—Th—Pyr—$R^2$ | Izl |
| $R^1$—Py—Th—Phe—Phe—$R^2$ | Izm |

In the compounds of the abovementioned formulae, the group Cy can contain a substituent X, which can be in the 1- or 4-position. Thus, for example, the compounds of the formula Il include those of the following part formulae Il' and Il":

Il'

Il"

(wherein the cyclohexane ring can additionally carry a further substituent X in the opposite position (4- or 1-position) of the cyclohexane ring and 1 to 4 further F atoms).

In this context, compounds of the above formulae I and Ib to Ie, Ibb, Icb, Il to Iq and Izc to Izh in which the radical Cy is, in each case, (1)

(2)

are furthermore particularly preferred.

Those stereoisomers in which the groups carrying the radicals $R^1$ and/or $R^2$ are in the trans-position relative to one another while the substituent X is in the cis-position relative to the opposite group are preferred. Thus, for example, the following stereoisomers of the compounds of the formula II' are preferred:

The abovementioned compounds of the formulae I and Ia to Izm each include the two possible pyridine derivatives with position isomerism, those of the formula I being, for example, the 2—[$R^1$—($A^1$—$Z^1$-

$)_m$—$(A^2$—$Z^2)_n$]—5—[Th—$(Z^3$—$A^3)_p$—$R^3$]-pyridines and the 5-[$R^1$—$(A^1$—$Z^1)_m$ $(A^2$—$Z^2)_n$]—2-[Th—$(Z^3$—$A^3)_p$—$R^3$]-pyridines, and those of the formula Ia accordingly being the 2—$R^1$—5-(Th—$R^2$)-pyridines and the 5—$R^1$—2-(Th—$R^2$)-pyridines.

Those of the abovementioned formulae which contain one or more of the groups DiO, Pip and/or Pyr in each case include the two possible 2,5- and 1,4-position isomers. Thus, for example, the part formula Ibc includes the 2—$R^1$—5—$(Z^1$—Py—Th—$R^2$)—1,3-dioxanes and the 2—$(Z^1$—Py—Th—$R^2$)—5—$R^1$—1,3-dioxanes, and the part formula Ibd includes the 1—$R^1$—4—$(Z^1$—Py—Th—$R^2$)—piperidines and the 1—$(Z^1$—Py—Th—$R^2$)—4—$R^1$—pyridines.

The compounds of the formula I are prepared by methods which are known per se, such as those described in the literature (for example in the standard works, such as Houben-Weyl, Methoden der Organischen Chemie (Methods of Organic Chemistry), Georg-Thieme Verlag, Stuttgart; Organic Reactions, John Wiley & Sons, Inc., New York), and in particular under reaction conditions which are known and suitable for the reactions mentioned. It is also possible to utilize variants which are known per se and are not mentioned here in more detail.

If desired, the starting substances can also be formed in situ such that they are not isolated from the reaction mixture but are immediately reacted further to give the compounds of the formula I.

The compounds of the formula I can thus be prepared by reacting an organometallic compound of the formula II ($Q^1$=M, wherein M is one equivalent of a metal atom, preferably Li, or the MgHal group) with a halogen compound of the formula III ($Q^2$=F, Cl, Br or I), or by reacting a halogen compound of the formula II ($Q^1$=F, Cl, Br or I) with an organometallic compound of the formula III ($Q^2$=M), advantageously in the presence of an inert solvent, for example an ether, such as diethyl ether, diisopropyl ether, tetrahydrofuran (THF) or dioxane, and/or a hydrocarbon, such as hexane or cyclohexane, at temperatures between about 0° and 100°. The starting substances are either known, or they can be prepared analogously to known substances, for example by metallization or halogenation of compounds of the formula II ($Q^1$=H) or III ($Q^2$=H), and the halogen compounds can also be prepared from corresponding amines via the diazonium salts by the methods of Sandmeyer and Schiemann.

The compounds of the formula I can furthermore be obtained by reacting a diazonium salt of the formula II ($Q^1$=the diazonium salt group) or an N-nitroso-acylamine of the formula II ($Q^1$=the N-nitroso-acylamino group) with a compound of the formula III ($Q^2$=H), or by reacting a diazonium salt of the formula III ($Q^2$=the diazonium salt group) or an N-nitroso-acylamine of the formula III ($Q^2$=the N-nitroso-acylamino group) with a compound of the formula II ($Q^1$=H), advantageously using an excess of the compound II ($Q^1$=H), for example pyridine, or of the compound III ($Q^2$=H), for example thiophene, as the solvent at temperatures between about −10° and 80°. Suitable N-nitrosoacylamines are, for example, N-nitroso-alkanoylamines, wherein the alkanoyl group has 2–6 C atoms, for example N-nitrosoacetamides or N-nitroso-isobutyramides. The conditions of these reactions can be varied in different ways, such as is described, for example, in Organic Reactions, loc. cit., volume II, pages 224–261 (1944). The starting substances are either known, or they can be prepared analogously to known substances by methods which are known per se, and the N-nitrosoacylamines can be prepared, for example, by acylation of corresponding amines and subsequent nitrosation.

The compounds of the formula I can also be prepared by reducing a compound which otherwise corresponds to the formula I but contains one or more reducible groups and/or C—C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but can contain a cyclohexanone ring instead of a cyclohexane ring, and/or a —CO— group instead of a —CH$_2$— group, and/or a free or a functionally modified (for example in the form of its p-toluenesulfonate) OH group instead of an H atom.

Ketones can be reduced, for example, by the methods of Clemmensen (with zinc, zinc amalgam or tin and hydrochloric acid, advantageously in aqueous-alcoholic solution or in a heterogeneous phase with water/toluene at temperatures between about 80° and 120°) or Wolff-Kishner (with hydrazine, advantageously in the presence of alkali, such as KOH or NaOH, in a high-boiling solvent, such as diethylene glycol or triethylene glycol, at temperatures between about 100° and 200°) to give the corresponding compounds of the formula I containing alkyl groups and/or —CH$_2$CH$_2$— bridges.

Reductions with complex hydrides are furthermore possible. For example, arylsulfonyloxy groups can be removed reductively with LiAlH$_4$, and in particular p-toluenesulfonyloxymethyl groups can be reduced to methyl groups, advantageously in an inert solvent, such as diethyl ether or THF, at temperatures between about 0° and 100°. Double bonds can be hydrogenated (also in the presence of CN groups!) with NaBH$_4$ or tributyl-tin hydride in methanol; thus, for example, the corresponding cyclohexane derivatives are formed from 1-cyanocyclohexene derivatives.

Esters of the formula I ($R^1$ and/or $R^2$=—O—COR or $Z^1$ and/or $Z^2$=—CO—O— or —O—CO—) can also be obtained by esterification of corresponding carboxylic acids of the formulae R—COOH, $R^1$—$(A^1$—$Z^1)_m$—$A^2$—COOH, $R^1$—$(A^1$—$Z^1)_m$—Py—Th—COOH, HOOC—$(A^2$—$Z_2)_n$—Py—Th—$(Z^3$—$A^3)_p$—$R^2$ or HOOC—$A^3$—$R^2$ (or their reactive derivatives) with alcohols or phenols of the formulae HO—$(A^1$—$Z^1)_m$—Py—Th—$(Z^3$—$A^3)_p$—$R^2$, $R^1$—$(A^1$—$Z^1)_m$—$(A^2$—$Z^2)_n$—Py—Th—$(Z^3$—$A^3)_p$—OH, HO—$A^3$—$R^2$, $R^1$—$A^1$—OH or $R^1$—$(A^1$—$Z^1)_m$—$A^2$—OH (or their reactive derivatives).

Particularly suitable reactive derivatives of the carboxylic acids mentioned are the acid halides, in particular the chlorides and bromides, and furthermore the anhydrides, for example also mixed anhydrides of the formulae R—CO—O—COCH$_3$, $R^1$—$A^1$—CO—O—COCH$_3$ and the like, azides or esters, in particular alkyl esters with 1-4 C atoms in the alkyl group.

Possible reactive derivatives of the alcohols and phenols mentioned are, in particular, the corresponding metal alcoholates or phenolates, for example the corresponding sodium or potassium alcoholates or phenolates.

The esterification is advantageously carried out in the presence of an inert solvent. Highly suitable solvents re, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane. Water-immiscible solvents can at the same time advantageously be used for azeotropic removal by distillation of the water formed during the esterification. An excess of an organic base, for example pyridine, quinoline or triethylamine, can occasionally also be used as the solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reactions are as a rule ended after 15 minutes up to 48 hours.

Specifically, the reaction conditions for the esterification largely depend on the nature of the starting substances used. Thus, a free carboxylic acid is reacted as a rule with free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, bases which are of importance being, in particular, alkali metal hydroxides, such as sodium or potassium hydroxide, alkali metal carbonates or bicarbonates, such as sodium carbonate, sodium bicarbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or phenol into the sodium or potassium alcoholate or phenolate, for example by treatment with ethanolic sodium hydroxide solution or potassium hydroxide solution, isolating this product and suspending it in acetone or diethyl ether, together with sodium bicarbonate or potassium carbonate, with stirring, and adding a solution of the acid chloride or anhydride in diethyl ether, acetone or DMF to this suspension, advantageously at temperatures between about $-25°$ and $+20°$.

Dioxane derivatives of the formula I (wherein at least one of the groups $A^1$, $A^2$ and/or $A^3$ is a 1,3-dioxane-2,5-diyl group) are advantageously prepared by reaction of a corresponding aldehyde, for example of the formula $R^1-(A^1-Z^1)_m-CHO$, $R^1-(A^1-Z^1)_m-(A^2-Z^2)_n-Py-Th-Z^3-CHO$, $O=CH-Z^1-(A^2-Z^2)_m-Py-Th-(Z^3-A^3)_p-R^2$ or $O=CH-(Z^3-A^3)_p-R^2$ (or of one of its reactive derivatives with a corresponding 1,3-diol, for example of the formula $(HOCH_2)_2CH-(A^2-Z^2)-Py-Th-(Z^3-A^3)_p-R^2$, $(HOCH_2)_2-R^2$, $R^1-CH(CH_2OH)_2$ or $R^1-(A^1-Z^1)_m-(A^2-Z^2)_n-Py-Th-Z^3-CH(CH_2OH)_2$ (or one of its reactive derivatives) preferably in the presence of an inert solvent, such as benzene or toluene, and/or of a catalyst, for example a strong acid, such as sulfuric acid or benzene- or p-toluene-sulfonic acid, at temperatures between about 20° and about 150°, preferably between 80° and 120°. Suitable reactive derivatives of the starting substances are, above all, acetals, for example of the formula $R^1-(A^1-Z^1)_m-CH(OR^3)_2$, $R^1-(A^1-Z^1)_m-(A^2-Z^2)_n-Py-Th-Z^3-CH(OR^3)_2$, $(R^3O)_2CH-Z^1-(A^2-Z^2)_n-Py-Th-(Z^3-A^3)-R^2$, $(R^3O)_2CH-(Z^3-A^3)_p-R^2$, $R^1-(A^1-Z^1)_m-CH(CH_2O)_2CHR^4$, $R^1-(A^1-Z^2)_n-Py-Th-Z^3-CH(CH_2O)_2CHR^4$, $R^4CH(OCH_2)_2CH-Z^1-(A^2-Z^2)_n-Py-Th-(Z^3-A^3)-R^2$ or $R^4CH(OCH_2)_2CH-(Z^3-Z^3)_p-R^2$, wherein $R^3$ is alkyl with 1–4 C atoms, or two of the radicals $R^3$ together are also alkylene with 2 or 3 C atoms, and $R^4$ is H, alkyl with 1–4 C atoms or phenyl.

The aldehydes and 1,3-diols mentioned and their reactive derivatives are known in some cases and in some cases can be prepared without difficulty by standard methods of organic chemistry from compounds which are known from the literature. For example, the aldehydes can be obtained by oxidation of corresponding alcohols or by reduction of corresponding carboxylic acids or their derivatives, and the diols can be obtained by reduction of corresponding diesters.

To prepare nitriles of the formula I (wherein $R^1$ and/or $R^2$ are CN and/or wherein $A^1$, $A^2$ and/or $A^3$ are substituted by at least one CN group), corresponding acid amides, such as, for example those in which one of the radicals $R^1$ or $R^2$ is replaced by a $CONH_2$ group, can be dehydrated. The amides can be obtained, for example, from corresponding esters or acid halides by reaction with ammonia.

Examples of suitable dehydrating agents are inorganic acid chlorides, such as $SOCl_2$, $PCl_3$, $PCl_5$, $POCl_3$, $SO_2Cl_2$ and $COCl_2$, and furthermore $P_2O_5$, $P_2S_5$, $AlCl_3$ (for example as a double compound with NaCl) and aromatic sulfonic acids and sulfonic acid halides. The reaction here can be carried out in the presence or absence of an inert solvent at temperatures between about 0° and 150°; examples of possible solvents or bases, such as pyridine or triethylamine, aromatic hydrocarbons, such as benzene, toluene or xylene, and amides, such as DMF.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working up, the nitriles can be isolated directly.

Ethers of the formula I (wherein $R^1$ and/or $R^2$ are an alkyl group, in which one or two $CH_2$ groups can be replaced by O atoms, and/or wherein $Z^1$ and/or $Z^2$ and/or $Z^3$ are a $-OCH_2-$ or a $-CH_2O-$ group) can be obtained by etherification of corresponding hydroxy compounds, preferably corresponding phenols, the hydroxy compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This product can then be reacted with the corresponding alkyl halide or sulfonate or dialkylsulfate, advantageously in an inert solvent, such as acetone, 1,2-dimethoxyethane, DMF or dimethylsulfoxide, or an excess of aqueous or aqueous-alcoholic NaOH or KOH at temperatures between about 20° and 100°.

To prepare chlorine or bromine compounds of the formula I (wherein $R^1$ and/or $R^2$ are Cl or Br), a corresponding compound of the formula I (wherein $R^1$ and/or $R^2$ are H) can be treated with chlorinating or brominating agent, advantageously with elemental chlorine or bromine, in an inert solvent, such as $CCl_4$, at temperatures between 0° and 70°.

To prepare nitriles of the formula I (wherein $R^1$ and/or $R^2$ are CN and/or wherein $A^1$, $A^2$ and/or $A^3$ are substituted by at least one CN group), corresponding chlorine or bromine compounds of the formula I (wherein $R^1$ and/or $R^2$ are Cl or Br and/or wherein $A^1$, $A^2$ and/or $A^3$ are substituted by at least one Cl or Br atom) can also be reacted with a cyanide, advantageously with a metal cyanide, such as NaCN, KCN or $Cu_2(CN)_2$, for example in the presence of pyridine in an inert solvent, such as DMF or N-methylpyrrolidone, at temperatures between 20° and 200°.

A base of the formula I can be converted into the associated acid addition salt with an acid. Acids which can be used for this reaction are inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono- or -disulfonic acid and lauryl-sulfuric acid.

Conversely, it is possible to liberate the base of the formula I from an acid addition salt of a compound of the formula I by treatment with a base, for example with a strong inorganic base, such as KOH or NaOH.

The dielectrics according to the invention consist of 2 to 15, preferably 3 to 12, components, including at least one compound of the formula I. The other constituents are preferably selected from the nematic or nematogenic substances, in particular the known substances, from the classes of azoxybenzenes, benzylideneanilines, biphenyls, terphenyls, phenyl- or cyclohexyl-benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrmidines, phenyl- or cyclohexyl-dioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds which are suitable as constituents of liquid crystal dielectrics of this type can be characterized by the formula IV $$R'—L—G—E—R'' \qquad \text{IV}$$

wherein L and E are each a carbocyclic or heterocyclic ring system from the group formed by 1,4-disubstituted benzene or cyclohexane rings, 4,4'-disubstituted biphenyl, phenylcyclohexane or cyclohexylcyclohexane systems, 2,5-disubstituted pyrimidine or 1,3-dioxane rings, 2,6-disubstituted naphthalene, di- or tetra-hydronaphthalene, quinazoline and tetrahydroquinazoline, G is

—CH=CH—

—CH=CY—

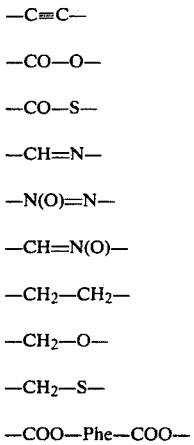

or a C—C single bond, Y is halogen, preferably chlorine, or —CN, and R' and R'' are alkyl, alkoxy, alkanoyloxy or alkoxycarbonyloxy with up to 18, preferably up to 8, carbon atoms, or one of these radicals is also CN, NC, $NO_2$, $CF_3$, F, Cl or Br.

In most of these compounds, R' and R'' differ from one another, one of these radicals usually being an alkyl or alkoxy group. However, other variants of the envisaged substituents can also be used. Many such substances or also mixtures thereof are commercially available.

The dielectrics according to the invention contain about 0.1 to 100%, preferably 10 to 100%, of one or more compounds of the formula I.

The dielectrics according to the invention are prepared in a manner which is customary per se. As a rule, the components are dissolved in one another, advantageously at elevated temperature.

The liquid crystal dielectrics according to the invention can be modified by suitable additives such that they can be used in all the types of liquid crystal display elements which have hitherto been disclosed.

Such additives are known to the expert and are described in detail in the literature. It is possible to add, for example, conductive salts, preferably ethyldimethyldodecyl-ammonium 4-hexyloxybenzoate, tetrabutylammonium tetraphenylboranate or complex salts of crown ethers (compare, for example, I. Haller et al., Mol. Cryst. Liq. Cryst. volume 24, pages 249–258 (1973)), for improving the conductivity, dichroic dyestuffs for the preparation of colored guest/host systems, or substances for modifying the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the examples, m.p. is the melting point and c.p. is the clear point of a liquid crystal substance.

"Customary working up" means: water is added, the mixture is extracted with methylene chloride, the phases are separated, the organic phase is dried and evaporated and the product is purified by crystallization and/or chromatography.

EXAMPLE 1

8.4 g of thiophene are dissolved in 300 ml of diethyl ether, and 68 ml of a 1.6M $C_4H_9Li$ solution in hexane are added at 0°, under $N_2$. After the mixture has been stirred for 2 hours, a solution of 16.8 g of 2-fluoro-5-pentylpyridine (obtainable from 3-pentylpyridine by amination to 2-amino-5-pentylpyridine and a subsequent Schiemann reaction) in 100 ml of diethyl ether is added and the mixture is warmed at 35° for 2 hours and poured onto ice to give, after customary working up, 2-(5-pentyl-2-pyridyl)-thiophene.

The following compounds are obtained analogously:
2-(5-ethyl-2-pyridyl)-thiophene
2-(5-propyl-2-pyridyl)-thiophene
2-(5-butyl-2-pyridyl)-thiophene
2-(5-hexyl-2-pyridyl)-thiophene
2-(5-heptyl-2-pyridyl)-thiophene
2-(5-octyl-2-pyridyl)-thiophene and
2-(5-pentadecyl-2-pyridyl)-thiophene.

EXAMPLE 2

24.8 g of N-(2-pentyl-5-pyridyl)-isobutyramide (boiling point 167°-171°/0.27 bar; obtainable by reacting 2-chloro-5-nitropyridine with Na-2-butylmalonic acid diethyl ester to give 2-(5-nitro-2-pyridyl)-2-butylmalonic acid diethyl ester, hydrolysis and decarboxylation to give 2-pentyl-5-nitropyridine, hydrogenation on 10% strength Pd-C in methanol at 40°-50° under 1 bar to give 2-pentyl-5-aminopyridine and acylation with isobutyric anhydride) are dissolved in a mixture of 110 ml of acetic acid and 50 ml of acetic anhydride, 49 g of anhydrous potassium acetate are added, and a solution of 6.9 g of nitrosyl chloride in 27 ml of acetic anhydride is then added at 0°. N-nitroso-N-(2-pentyl-5-pyridyl)-isobutyramide is formed as the intermediate and is not isolated. After the mixture has been stirred at 0° for 15 minutes, it is poured onto ice and extracted five times with 140 ml of thiophene each time. The phases are separated, the organic phase is kept at 0° and made into a slurry with 22 g of $K_2CO_3$ and 35 g of $Na_2SO_4$, and the slurry is decanted. The organic phase is warmed at 50° and, when the evolution of gas has ended, boiled for 2 hours, and evaporated and the residue is separated on silica gel using toluene. 2-(2-Pentyl-5-pyridyl)-thiophene, boiling point 180°-185°/0.013 bar, c.p. −45° is obtained; a little 3-(2-pentyl-5-pyridyl)-thiophene, boiling point 170°-180°/0.015 bar, c.p. −80°, is also formed.

The following compounds are obtained analogously:
2-(2-propyl-5-pyridyl)-thiophene
3-(2-propyl-5-pyridyl)-thiophene
2-(2-butyl-5-pyridyl)-thiophene
3-(2-butyl-5-pyridyl)-thiophene
2-(2-hexyl-5-pyridyl)-thiophene
3-(2-hexyl-5-pyridyl)-thiophene
2-(2-heptyl-5-pyridyl)-thiophene
3-(2-heptyl-5-pyridyl)-thiophene
2-(2-octyl-5-pyridyl)-thiophene
3-(2-octyl-5-pyridyl)-thiophene
2-(2-pentyl-5-pyridyl)-5-methyl-thiophene
2-[2-(trans-4-propylcyclohexyl)-5-pyridyl]-thiophene
2-[2-(trans-4-pentylcyclohexyl)-5-pyridyl]-thiophene
2-[2-(2-(trans-4-propylcyclohexyl)-ethyl)-5-pyridyl]-thiophene and
2-[2-(2-trans-4-methoxymethylcyclohexyl)-ethyl)-5-pyridyl]-thiophene.

EXAMPLE 3

A mixture of 2.73 g of 2-acetyl-4-(2-pentyl-5-pyridyl)-thiophene [m.p. 72°; obtainable by reacting 2-(2-pentyl-5-pyridyl)-thiophene with acetylchloride $SnCl_4$ in benzene], 1.6 g of 85% strength hydrazinehydrate solution, 1.6 g of KOH and 8 ml of triethylene glycol is boiled for 2 hours, heated at 195°, the water and hydrazinehydrate being distilled off, and cooled to give, after customary working up, 2-ethyl-5-(2-pentyl-5-pyridyl)-thiophene, boiling point 180°/0.07 mbar.

The following compounds can be obtained analogously, by reduction of corresponding ketones:
2-ethyl-5-(2-propyl-5-pyridyl)-thiophene
2-ethyl-5-(2-butyl-5-pyridyl)-thiophene
2-ethyl-5-(2-hexyl-5-pyridyl)-thiophene
2-ethyl-5-(2-heptyl-5-pyridyl)-thiophene
2-propyl-5-(2-propyl-5-pyridyl)-thiophene
2-propyl-5-(2-butyl-5-pyridyl)-thiophene
2-propyl-5-(2-pentyl-5-pyridyl)-thiophene
2-propyl-5-(2-hexyl-5-pyridyl)-thiophene
2-propyl-5-(2-heptyl-5-pyridyl)-thiophene
2-butyl-5-(2-propyl-5-pyridyl)-thiophene
2-butyl-5-(2-butyl-5-pyridyl)-thiophene
2-butyl-5-(2-pentyl-5-pyridyl)-thiophene
2-butyl-5-(2-hexyl-5-pyridyl)-thiophene
2-butyl-5-(2-heptyl-5-pyridyl)-thiophene
2-pentyl-5-(2-propyl-5-pyridyl)-thiophene
2-pentyl-5-(2-butyl-5-pyridyl)-thiophene
2-pentyl-5-(2-pentyl-5-pyridyl)-thiophene
2-pentyl-5-(2-hexyl-5-pyridyl)-thiophene
2-pentyl-5-(2-heptyl-5-pyridyl)-thiophene
2-hexyl-5-(2-propyl-5-pyridyl)-thiophene
2-hexyl-5-(2-butyl-5-pyridyl)-thiophene
2-hexyl-5-(2-pentyl-5-pyridyl)-thiophene
2-hexyl-5-(2-hexyl-5-pyridyl)-thiophene
2-hexyl-5-(2-heptyl-5-pyridyl)-thiophene
2-heptyl-5-(2-propyl-5-pyridyl)-thiophene
2-heptyl-5-(2-butyl-5-pyridyl)-thiophene
2-heptyl-5-(2-pentyl-5-pyridyl)-thiophene
2-heptyl-5-(2-hexyl-5-pyridyl)-thiophene and
2-heptyl-5-(2-heptyl-5-pyridyl)-thiophene.

EXAMPLE 4

20.5 g of 5-(2-Thienyl)-picolinic acid is boiled for 1 hour with 24 g of $SOCl_2$, the mixture is evaporated, the resulting crude acid chloride is dissolved in 150 ml of toluene, 8 ml of pyridine and 16.7 g of cis-4-cyano-4-propylcyclohexanol (obtainable by alkylation of 4-cyanocyclohexanol) are added and the mixture is boiled for 2 hours. After cooling and customary working up, 5-(2-thienyl)-picolinic acid cis-4-cyano-4-propylcyclohexyl ester is obtained.

The following compounds are obtained analogously with the corresponding cyclohexanols:

5-(2-thienyl)-picolinic acid cis-4-methyl-4-propylcyclohexyl ester
5-(2-thienyl)-picolinic acid cis-4-methoxy-4-propylcyclohexyl ester and
5-(2-thienyl)-picolinic acid cis-4-trifluoromethyl-4-propylcyclohexyl ester.

EXAMPLE 5

A mixture of 1.2 g of 2-propylpropane-1,3-diol, 2.59 g of 5-(2-pentyl-5-pyridyl)-2-formyl-thiophene (obtainable by formylation of 5-(2-pentyl-5-pyridyl)-thiophene via a Vilsmeier reaction), 0.01 g of p-toluenesulfonic acid and 15 ml of toluene is boiled for 3 hours, using a water separator, cooled, washed with water and evaporated. 5-(2-Pentyl-5-pyridyl)-2-(trans-5-propyl-1,3-dioxan-2-yl)-thiophene is obtained.

The following compounds are obtained analogously, by reacting the corresponding aldehydes with the corresponding diols:

5-(2-propyl-5-pyridyl)-2-(trans-5-propyl-1,3-dioxan-2-yl)-thiophene
5-(2-propyl-5-pyridyl)-2-(trans-5-butyl-1,3-dioxan-2-yl)-thiophene
5-(2-propyl-5-pyridyl)-2-(trans-5-pentyl-1,3-dioxan-2-yl)-thiophene
5-(2-propyl-5-pyridyl)-2-(trans-5-hexyl-1,3-dioxan-2-yl)-thiophene
5-(2-propyl-5-pyridyl)-2-(trans-5-heptyl-1,3-dioxan-2-yl)-thiophene
5-(2-butyl-5-pyridyl)-2-(trans-5-propyl-1,3-dioxan-2-yl)-thiophene
5-(2-butyl-5-pyridyl)-2-(trans-5-butyl-1,3-dioxan-2-yl)-thiophene
5-(2-butyl-5-pyridyl)-2-(trans-5-pentyl-1,3-dioxan-2-yl)-thiophene
5-(2-butyl-5-pyridyl)-2-(trans-5-hexyl-1,3-dioxan-2-yl)-thiophene
5-(2-butyl-5-pyridyl)-2-(trans-5-heptyl-1,3-dioxan-2-yl)-thiophene
5-(2-pentyl-5-pyridyl)-2-(trans-5-butyl-1,3-dioxan-2-yl)-thiophene
5-(2-pentyl-5-pyridyl)-2-(trans-5-pentyl-1,3-dioxan-2-yl)-thiophene
5-(2-pentyl-5-pyridyl)-2-(trans-5-hexyl-1,3-dioxan-2-yl)-thiophene
5-(2-pentyl-5-pyridyl)-2-(trans-5-heptyl-1,3-dioxan-2-yl)-thiophene
5-(2-hexyl-5-pyridyl)-2-(trans-5-propyl-1,3-dioxan-2-yl)-thiophene
5-(2-hexyl-5-pyridyl)-2-(trans-5-butyl-1,3-dioxan-2-yl)-thiophene
5-(2-hexyl-5-pyridyl)-2-(trans-5-pentyl-1,3-dioxan-2-yl)-thiophene
5-(2-hexyl-5-pyridyl)-2-(trans-5-hexyl-1,3-dioxan-2-yl)-thiophene
5-(2-hexyl-5-pyridyl)-2-(trans-5-heptyl-1,3-dioxan-2-yl)-thiophene
5-(2-heptyl-5-pyridyl)-2-(trans-5-propyl-1,3-dioxan-2-yl)-thiophene
5-(2-heptyl-5-pyridyl)-2-(trans-5-butyl-1,3-dioxan-2-yl)-thiophene
5-[2-heptyl-5-pyridyl)-2-(trans-5-pentyl-1,3-dioxan-2-yl)-thiophene
5-(2-heptyl-5-pyridyl)-2-(trans-5-hexyl-1,3-dioxan-2-yl)-thiophene and
5-(2-heptyl-5-pyridyl)-2-(trans-5-heptyl-1,3-dioxan-2-yl)-thiophene.

EXAMPLE 6

65 g of POCl$_3$ are added dropwise to a solution of 31.6 g of 2-trans-4-propylcyclohexyl)-5-(5-carbamoyl-2-thienyl)-pyridine (obtainable from the acid chloride with NH$_3$) in 500 ml of DMF at 50°, with stirring. After the mixture has been stirred for a further hour, it is poured onto ice and worked up in the customary manner to give 2-(trans-4-propylcyclohexyl)-5-(5-cyano-2-thienyl)-pyridine.

The following compounds are obtained analogously, by splitting off water from the corresponding amides:
2-p-cyanophenyl-5-(2-thienyl)-pyridine 2-(4'-cyano-4-biphenylyl)-5-(2-thienyl)-pyridine and 2-(5-cyano-2-pyrimidyl)-5-(2-thienyl)-pyridine.

EXAMPLE 7

A solution of 37.6 g of 1-pentyl-cis-4-[5-(2-thienyl)-2-pyridyl]-cyclohexane-r-1-carbonyl chloride [obtainable by reacting 4-]5-(2-thienyl)-2-pyridyl)]-cyclohexanone with pentyl-Li and subsequent hydrolysis to give 1-pentyl-4-[5 -(2-thienyl)-2-pyridyl]-cyclohexanol, reacting with K and then with CO$_2$ to give 1-pentyl-cis-4-[5-(2-thienyl)-2-pyridyl]-cyclohexane-r-1-carboxylic acid and reaction with SOCl$_2$] and 8 g of sulfamide in 500 ml of tetramethylene sulfone is heated at 120° for 4 hours and evaporated and the residue is worked up in the customary manner. r-1-Cyano-1-pentyl-cis-4-[5-(2-thienyl)-2-pyridyl]-cyclohexane is obtained.

EXAMPLE 8

A mixture of 15.3 g of 2-(2-p-hydroxyphenyl-5-pyridyl)-thiophene, 6.9 g of K$_2$CO$_3$, 25 g of hexyl iodide and 250 ml of DMF is heated at 80° C. for 16 hours, with stirring, and then cooled and worked up in the customary manner. 2-(2-p-Hexoxyphenyl-5-pyridyl)-thiophene is obtained.

EXAMPLE 9

4.8 g of NaH and 27.8 g of CH$_3$I are added to a solution of 32.9 g of r-1-hydroxy-1-pentyl-cis-4-[5-(2-thienyl)-2-pyridyl]-cyclohexane [obtainable by oxidation of 4-[5-(2-thienyl)-2-pyridyl]-cyclohexanol with CrO$_3$ to give the ketone, reaction with pentyl-MgBr and hydrolysis] in 280 ml of 1,2-dimethoxyethane. After the mixture has been heated at 70° for 5 hours, it is cooled, water is added and the mixture is worked up in the customary manner to give r-1-methoxy-1-pentyl-cis-4-[5-(2-thienyl)-2-pyridyl]-cyclohexane.

EXAMPLE 10

7.3 g of chlorine are passed in, or 17 g of bromine are added dropwise, with stirring, to a solution of 23.1 g of 2-(2-pentyl-5-pyridyl)-thiophene in 40 ml of CCl$_4$ at 20°. After the mixture has been left to stand for 1 hour, it is warned at 50° for 2 hours, washed with dilute sodium hydroxide solution and worked up in the customary manner to give 5-chloro-2-(2-pentyl-5-pyridyl)-thiophene, m.p. 32°, c.p. 18° (or 5-bromo-2-(2-pentyl-5-pyridyl)-thiophene).

The following compounds are obtained by halogenation:
5-chloro-2-(2-propyl-5-pyridyl)-thiophene
5-chloro-2-(2-butyl-5-pyridyl)-thiophene 5-chloro-2-(2-hexyl-5-pyridyl)-thiophene
5-chloro-2-(2-heptyl-5-pyridyl)-thiophene
5-bromo-2-(2-propyl-5-pyridyl)-thiophene
5-bromo-2-(2-butyl-5-pyridyl)-thiophene
5-bromo-2-(2-hexyl-5-pyridyl)-thiophene and
5-bromo-2-(2-heptyl-5-pyridyl)-thiophene.

EXAMPLE 11

A mixture of 26.6 g of 5-chloro-2-(2-pentyl-5-pyridyl)-thiophene, 10 g of $Cu_2(CN)_2$, 120 ml of pyridine and 60 ml of N-methylpyrrolidone is heated at 150° for 2 hours. It is cooled, a solution of 120 g of $FeCl_3.6 H_2O$ in 600 ml of 20% strength hydrochloric acid is added and the mixture is warmed at 70° C. for 1.5 hours, with stirring, and worked up in the customary manner to give 2-(2-pentyl-5-pyridyl)-thiophene-5-carbonitrile.

The following compounds are obtainable analogously from the corresponding chlorine or bromine compounds:
2-(2-propyl-5-pyridyl)-thiophene-5-carbonitrile
2-(2-butyl-5-pyridyl)-thiophene-5-carbonitrile
2-(2-hexyl-5-pyridyl)-thiophene-5-carbonitrile and
2-(2-heptyl-5-pyridyl)-thiophene-5-carbonitrile.

Examples of dielectrics according to the invention containing at least one compound of the formula I follow:

EXAMPLE A

A mxxture of
21% of 2-(2-pentyl-5-pyridyl)-thiophene,
22% of p-trans-4-butylcyclohexyl-benzonitrile,
14% of 4-ethyl-4'-cyanobiphenyl,
18% of 4-butyl-4'-cyanobiphenyl,
16% of 4-cyano-4'-(trans-4-pentylcyclohexyl)-biphenyl and
9% of 4-(trans-4-pentylcyclohexyl)-4'-(trans-4-propylcyclohexyl)-biphenyl
has a c.p. of 62°.

EXAMPLE B

A mixture of
15% of 2-(2-pentyl-5-pyridyl)-thiophene-5-carbonitrile,
15% of p-trans-4-propylcyclohexyl-benzonitrile,
11% of p-trans-4-butylcyclohexyl-benzonitrile,
21% of p-trans-4-pentylcyclohexyl-benzonitrile,
21% of 4-ethyl-4'-(trans-4-pentylcyclohexyl)-biphenyl,
12% of 4-(trans-4-pentylcyclohexyl)-4'-(trans-4-propylcyclohexyl)-biphenyl and
5% of 4-cyano-4'-(trans-4-pentylcyclohexyl)-biphenyl
has a c.p. of 90°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystalline phase comprising at least two liquid crystalline compounds, wherein at least one liquid crystalline compound is a pyridylthiophene of the formula

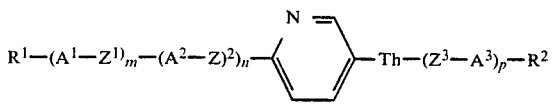

wherein
Th is a thiophene-2,4- or -2,5-diyl ring,
$R^1$ and $R^2$ are each independently an alkyl group of 1–15 C atoms, $C_{1-15}$-alkyl in which one or two non-adjacent $CH_2$ groups are replaced by O atoms, F, Cl, Br, CN or —O—COR, and one of $R^1$ or $R^2$ can also be H,
$A^1$, $A^2$ and $A^3$ are each independently 1,4-phenylene, 1,4-cyclohexylene, 1,3-dioxane-2,5-diyl, piperidine-1,4-diyl, 1,4,-bicylo-(2,2,2,)-octylene or pyrimidine-2,5-diyl, or one of these groups substituted by 1-F atoms, or said 1,4-cyclohexylene or substituted 1,4-cyclohexylene group substituted in the 1-, 4- or 1- and 4-positions by alkyl, alkoxy, fluorinated alkyl or fluorinated alkoxy, each of 1–5 C atoms, F, Cl, Br or CN,
$Z^1$, $Z^2$ and $Z^3$ are each independently —CO—O—, —O—CO—, —CH$_2$CH$_2$—, —OCH$_2$—, —CH$_2$O— or a single bond,
(m+n+p) is 0, 1 or 2, and
R is alkyl of 1–5 C atoms,
or an acid addition salt of such a compound which is basic the ring

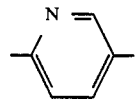

being designated Py.

2. A liquid crystalline phase of claim 1 of the formula $R^1$—Py—Th—$R^2$.

3. A liquid crystalline phase of claim 1 of the formula $R^1$—$A^1$—$Z^1$—Py—Th—$R^2$.

4. A liquid crystalline phase of claim 1 of the formula $R^1$—Py—Th—$Z^3$—$A^3$—$R^2$.

5. A liquid crystalline phase of claim 1 of the formula $R^1$—$A^1$—$Z^1$—Py—Th—$Z^3$—$A^3$—$R^2$.

6. A liquid crystalline phase of claim 1 of the formula $R^1$—$A^1$—$Z^1$—$A^2$—$Z^2$—Py—Th—$R^2$.

7. A liquid crystalline phase of claim 1 of the formula $R^1$—Phe—$Z^1$—Py—Th—$R^2$ $R^1$—Cy—$Z^1$—Py—Th—$R^2$ $R^1$—Dio—$Z^1$—Py—Th—$R^2$ $R^1$—Pip—$Z^1$—Py—Th—$R^2$ $R^1$—Bic—$Z^1$—Py—Th—$R^2$ $R^1$—Pyr—$Z^1$—Py—Th—$R^2$ $R^1$—Py—Th—$Z^3$—Phe—$R^2$ R¹—Py—Th—Z³—Cy—R²

R¹—Py—Th—Z³—Dio—R²

R¹—Py—Th—Z³—Pip—R²

R¹—Py—Th—Z³—Bic—R²

R¹—Py—Th—Z³—Pyr—R² wherein "Phe" is 1,4-phenylene, "Cy" is 1,4-cyclohexylene, "Dio" is 1,3-dioxane-2,5-diyl, "Bic" is bicyclo(2,2,2)-octylene, "Pip" is piperidine-1,4-diyl and "Pyr" is pyrimidine-2,5-diyl, each unsubstituted or substituted.

8. A liquid crystalline phase of claim 1 of the formula

R¹—Phe—Z¹—Py—Th—R²

R¹—Cy—Z¹—Py—Th—R²

R¹—Py—Th—Z³—Phe—R² wherein "Phe" is 1,4-phenylene, "Cy" is 1,4-cyclohexylene, each unsubstituted or substituted.

9. A liquid crystalline phase of claim 1 wherein R¹ and R² are alkyl or alkoxy.

10. A liquid crystalline phase of claim 1 wherein A¹, A² and A³ are cyclohexylene or phenylene.

11. A liquid crystalline phase of claim 1 wherein at least one of A1, A2 or A3 is 1-X-1,4-cyclohexylene, otherwise unsubstituted or substituted, wherein X is alkyl, alkoxy, fluorinated alkyl or fluorinated alkoxy each of 1-5 C atoms, F, Cl, Br or CN.

12. A liquid crystalline of claim 11 wherein X is CN, CH₃, CH₃O or CF₃.

13. A liquid crystalline phase of claim 1 wherein Z¹, Z² and Z³ are a single bond, —CO—O— or —O—CO—.

14. A liquid crystalline phase of claim 1 wherein m+n+p=O.

15. A liquid crystalline phase of claim 9 wherein all alkyl or alkoxy groups are straight chained.

16. A liquid crystalline phase of claim 1 of the formula

R¹—Phe—Py—Th—R²

R¹—Phe—CO—O—Py—Th—R²

R¹—Phe—O—CO—Py—Th—R²

R¹—Phe—CH₂CH₂—Py—Th—R²

R¹—Phe—O—CH₂—Py—Th—R²

R¹—Phe—CH₂—O—Py—Th—R²

R¹—Cy—Py—Th—R²

R¹—Cy—CO—O—Py—Th—R²

R¹—Cy—O—CO—Py—Th—R²

R¹—Cy—CH₂CH₂—Py—Th—R²

R¹—Cy—O—CH₂—Py—Th—R²

R¹—Cy—CH₂—O—Py—Th—R²

R¹—Dio—Py—Th—R²

R¹—Pip—Py—Th—R²

R¹—Bic—Py—Th—R²

R¹—Phe—Phe—Py—Th—R²

R¹—Py—Th—Phe—R²

R¹—Py—Th—CO—O—Phe—R²

R¹—Py—Th—O—CO—Phe—R²

R¹—Py—Th—CH₂CH₂—Phe—R²

R¹—Py—Th—O—CH₂—Phe—R²

R¹—Py—Th—CH₂—O—Phe—R²

R¹—Py—Th—Cy—R²

R¹—Py—Th—CO—O—Cy—R²

R¹—Py—Th—O—CO—Cy—R²

R¹—Py—Th—CH₂CH₂—Cy—R²

R¹—Py—Th—O—CH₂—Cy—R²

R¹—Py—Th—CH₂—O—Cy—R²

R¹—Py—Th—Dio—R²

R¹—Py—Th—Pip—R²

R¹—Py—Th—Bic—R²

R¹—Py—Th—Pyr—R²

R¹—Py—Th—Phe—Phe—R² wherein "Phe" is 1,4-phenylene, "Cy" is 1,4-cyclohexylene, "Dio" is 1,3-dioxane-2,5-diyl, "Bic" is bicyclo(2,2,2)-octylene, "Pip" is piperidine-1,4-diyl and "Pyr" is pyrimidine-2,5-diyl, each unsubstituted or substituted.

17. A liquid crystalline phase of claim 16 containing at least one cyclohexylene unit of the formula wherein the cyclohexane ring can additionally carry a further substituent X in the opposite position (4- or 1-position) of the cyclohexane ring and 1 to 4 further F atoms, and wherein X is alkyl, alkoxy, fluorinated alkyl or fluorinated alkoxy each of 1-5 C atoms, F, Cl, Br or CN.

18. A liquid crystalline phase of claim 1 containing at least one ring of the formula 19. A liquid crystalline phase of claim 1, of the formula R¹—Py—Th—R² wherein R² is F, Cl or Br.

20. A liquid crystalline compound of claim 19 of the formula

R¹—Py—Th—Cl.

21. A liquid crystaline phase of claim 1, wherein Th is 2,4-diyl.

22. A liquid crystalline phase of claim 1, wherein m+n=0.

23. A liquid crystalline phase of claim 1, wherein $A^1$, $A^2$ and $A^3$ are each independently 1,4-cyclohexylene, 1,3-dioxane-2,5-diyl,piperidine-1,4-diyl,1,4-bicyclo-(2,2,2)-octylene or pyrimidine-2,5-diyl, or one of these groups substituted by 1–4 F atoms, or said 1,4-cyclohexylene or substituted 1,4-cyclohexylene group substituted in the 1-, 4- or 1- and 4-positions by alkyl, alkoxy, fluorinated alkyl, fluorinated alkoxy, each of 1-5 C atoms, F, Cl, Br or CN.

24. A liquid crystalline phase of claim 1, wherein $Z^1$, $Z^2$ and $Z^3$ are each independently —CO—O—, —O—CO—, —CH₂CH₂—, —OCH₂— or —CH₂O—.

25. A liquid crystalline phase of claim 1, wherein $R^1$ is alkyl and $R^2$ is Cl.

* * * * *